(12) United States Patent
Krystek et al.

(10) Patent No.: US 8,740,865 B2
(45) Date of Patent: Jun. 3, 2014

(54) OSTOMY APPLIANCE WEAR TIME PREDICTION

(75) Inventors: Paul N Krystek, Highland, NY (US); Mark B Stevens, Austin, TX (US); John David Wilson, Houston, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/484,334

(22) Filed: May 31, 2012

(65) Prior Publication Data

US 2013/0324952 A1 Dec. 5, 2013

(51) Int. Cl.
*A61F 5/445* (2006.01)

(52) U.S. Cl.
USPC .............. 604/318; 602/41; 340/657; 340/605

(58) Field of Classification Search
None
See application file for complete search history.

(56) References Cited

U.S. PATENT DOCUMENTS

| | | | |
|---|---|---|---|
| 5,250,042 A | 10/1993 | Torgalkar et al. | |
| 6,171,289 B1 | 1/2001 | Millot et al. | |
| 6,437,038 B1 | 8/2002 | Chen | |
| 6,752,785 B2 | 6/2004 | Van Antwerp et al. | |
| 7,670,289 B1 | 3/2010 | McCall | |
| 7,722,585 B2 | 5/2010 | Falconer et al. | |
| 8,118,797 B2 | 2/2012 | Giori et al. | |
| 8,436,121 B2 | 5/2013 | Lam et al. | |
| 2003/0009131 A1* | 1/2003 | Van Antwerp et al. | 604/111 |
| 2007/0078418 A1 | 4/2007 | May et al. | |
| 2010/0030167 A1* | 2/2010 | Thirstrup et al. | 604/318 |

FOREIGN PATENT DOCUMENTS

WO  WO2011113442  9/2011

OTHER PUBLICATIONS

Anonymous; "FepiBlue"—A Wearable Febrile/Epilepsy Alert Wireless Sensor Belt for a Human Being, Feb. 3, 2012.
Anonymous; "Method for an on-package measurement system for predicting reliability"; Mar. 16, 2005.
Lindsay, J., et al.; "Improved Wearable Sensor Systems", Jul. 23, 2004.
Baars, Max; "The theremin—how it works", retrieved on May 9, 2012, from http://www.thereminvox.com.
Stomabags.Com; "Comfort-63", retrieved on May 9, 2012, from http://www.stomabags.com.
Koolostomy.Com; "The fly pouch cover", retrieved on May 9, 2012, from http://www.koolostomy.com.
Ostomy; "UOAA Colostomy Guide"; Retrieved on Jul. 31, 2013 from www.ostomy.org/ostomy_info/pubs/ColostomyGuide.pdf.
Crohnsforum; "Failing Colostomy Bags"; Retrieved on Jul. 31, 2013 from http://www.crohnsforum.com/showthread.php?t=33213.
Hollister; "Routine Care of Your Ostomy"; Retrieved on Jul. 31, 2013 from www.hollister.com.

\* cited by examiner

*Primary Examiner* — Leslie Deak
*Assistant Examiner* — Sara Sass
(74) *Attorney, Agent, or Firm* — Robert H. Frantz; Jeffrey S. LaBaw; Parashos Kalaitzis

(57) ABSTRACT

Use of and performance of ostomy appliances are enhanced by providing one or more sensors to an ostomy pouch; collecting sensor data by sensors to form a history of events impinging on the ostomy pouch and conditions of the pouch over time; comparing the sensor data to historical sensor data for a similar ostomy pouch to predict a reduction in nominal wear time; and notifying a user of the predicted reduction in nominal wear time.

20 Claims, 5 Drawing Sheets

*Prior Art*

(a)

(b)

OSTOMY APPLIANCE WEAR TIME PREDICTION

FIELD OF THE INVENTION

The invention generally relates to biosensors for improving the usage of and performance by ostomy appliances.

BACKGROUND OF INVENTION

An ostomy is a medical appliance that is used to collect body waste output following removal of a portion of a patient's intestine. Depending on the area of the intestinal removal, the name of the appliance may vary, such as colostomy, ileostomy and urostomy.

Generally speaking, an ostomy appliance is an external collection reservoir, usually in the form of a collapsible or expandable bag. Through a surgical procedure, an opening is formed in a patient's abdomen, through which a connection to intestine is made with a flange. The ostomy appliance is then attached, often using an adhesive ring or wafer applied to the skin of the abdomen. Waste and products from the patient's intestine are then redirected into the ostomy appliance, where it is collected until the bag is discarded and replaced with an empty bag. There are a number of variations of ostomy bags in use today, some of which are meant for longer term wear and can be emptied (reducing the number of times the adhesive must be removed from the skin), and some of which are meant for shorter term wear (bags are filled, removed, sealed, discarded and a new bag is attached).

Ostomy appliances have been improved over the years, and they are quite effective. Their form and shape have been refined such that it is unlikely that an observer would notice that a patient is wearing an ostomy appliance, which allows many ostomy patients to live a normal lifestyle with proper attention and maintenance to the appliance.

SUMMARY OF EXEMPLARY EMBODIMENTS OF THE INVENTION

Use of and performance of ostomy appliances are enhanced by providing one or more sensors to an ostomy pouch; collecting sensor data by sensors to form a history of events impinging on the ostomy pouch and conditions of the pouch over time; comparing the sensor data to historical sensor data for a similar ostomy pouch to predict a reduction in nominal wear time; and notifying a user of the predicted reduction in nominal wear time.

BRIEF DESCRIPTION OF THE DRAWINGS

The description set forth herein is illustrated by the several drawings.

DETAILED DESCRIPTION OF EXEMPLARY EMBODIMENT(S) OF THE INVENTION

Figure 1:
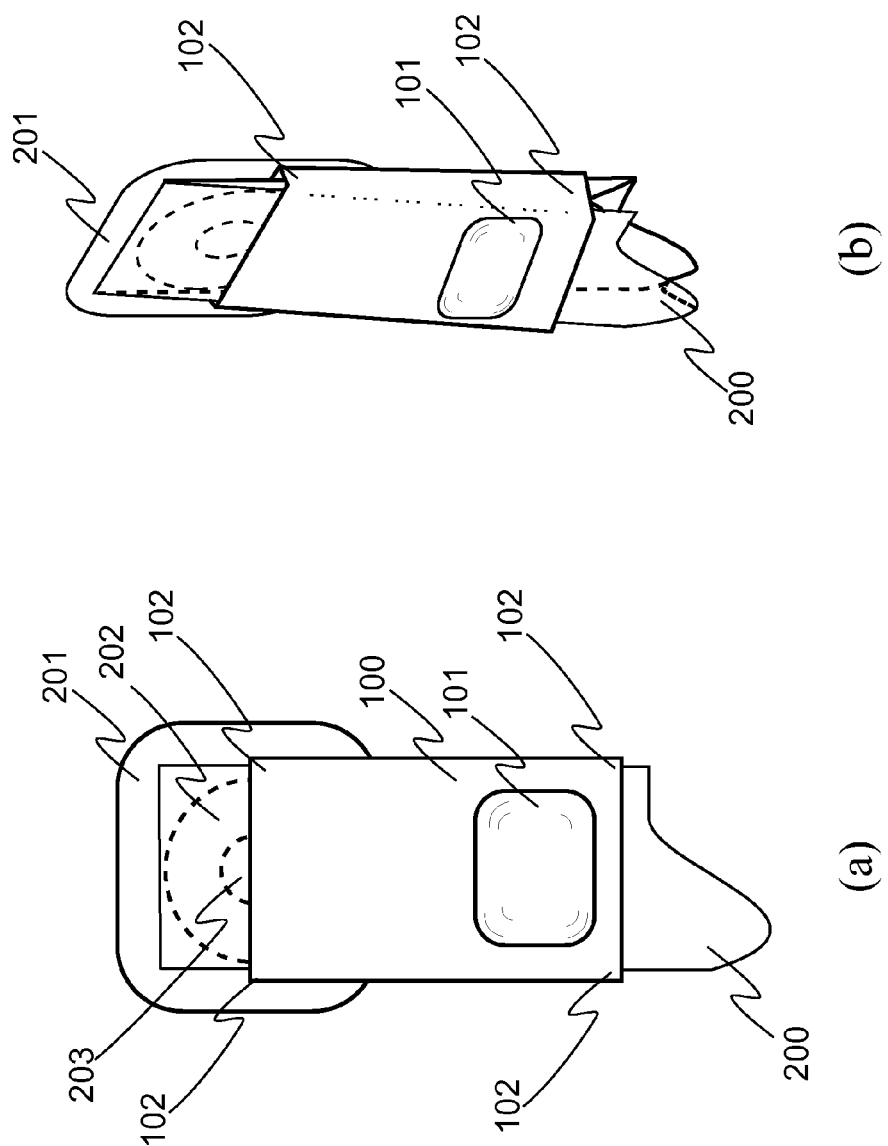
FIG. 1 depicts a sleeve-style embodiment according to the present invention.

The inventors of the present and the related invention have recognized problems not yet recognized by those skilled in the relevant arts regarding ostomy appliances, their performance and their methods of use, especially with respect to "wear time" (e.g. the time that an ostomy bag is used for its purpose).

Despite the improvements to ostomy appliances over the years, the present inventors have realized that there remains an unrecognized and unsolved problem in the art that plagues ostomy patients. The appliance has a wear time which is not only limited by the capacity of the device, but also by (a) the varying amount of waste collected from the patient, (b) failure of the adhesion to the patient's abdomen, and (c) failure (rupture, leak, etc.) of the device's containing function. And, these conditions may effect each other, for example, a full bag is more likely to rupture or lose adhesion than a new, nearly-empty bag.

Usually there are very limited warning signs that these conditions are imminent. Unexpectedly reaching capacity or failure of an appliance may occur at an inconvenient time and place. The patient may not have a replacement device with him or her, and there may not be a suitable private place to change the appliance.

Such situations are not only a threat to the health of the patient and a possible public health issue (proper disposal of the used bags is essential), but these situations also may be quite embarrassing for patients. The potential for such embarrassment may lead to anxiety in the patient, thereby leading to self-restriction of activities and lifestyle, which counters some of the benefits achieved through the technical advances in the ostomy products.

Existing technologies attempt to provide leak detection via moisture or capacitance detectors built into the flange, but the approach of leak detection only addresses a problem after it has occurred. While this may reduce the chance of being embarrassed by giving the wearer notice that a leak is already occurring, it does little to help prevent such situations and does not allay fear and anxiety of such situations arising. Once a leak develops the patient has very little time to correct the situation before catastrophic failure occurs. In addition, the patient may not be in a place where the appliance can be changed or the patient may not have an appliance on hand.

These problems are also exacerbated by patients' tendency to try to get the longest possible wear time out of each bag due to the high cost of the bags, so proactive or "early" changing of bags is not generally a desirable solution to these problems, either.

Embodiments of the present invention provide a method and system to give the patient an early warning system that the ostomy appliance may be nearing end of life, and that it is time to change regardless of it appearing superficially to be reliable.

The present inventors realized that, over time and with sufficient experience with a particular ostomy product, a patient may develop a sense of the usual wear time for a particular brand and model appliance. Unfortunately this is only a guideline and various events can shorten this time considerably. Examples of such events which may shorten wear time are:

higher than normal activity, i.e. a lot of trunk activity
    high ambient temperature
    high ambient moisture (sweating, damp clothes, etc.)
    low moisture (dry or parching climate)
    contents of pouch (presence of liquid)

pouch overpressure condition
pouch load over time
traumatic physical contact (bumping, jabbing, twisting, binding, etc.)
patient orientation (vertical, horizontal, etc.)

Embodiments of the present invention provide an outer sleeve which is placed over, around, or in contact with the ostomy bag or reservoir. The sleeve has integrated sensors that monitor the conditions and events that happen to the appliance over time. By tracking this information, historical conditions and events are collected. Then, the historical data can be used to predict wear time, future failures, likely full times, etc., based on conditions and events that have and are occurring to a current bag and correlating those to historical events, conditions and wear times. In this manner, an accurate picture can be created of estimated remaining life of the appliance, thereby providing the patient with a proactive, predictive tool to avoid failures, leaks, and unexpected full conditions, which in turn will relieve anxiety, avoid embarrassment, and benefit the health of the patient as well as public health by allowing bag changes under appropriate conditions. And, by minimizing the unused portion of a bag's useful life, costs are minimized compared to proactively exchanging bags based on guesses of wear time in an over-abundance of caution.

Figure 2:
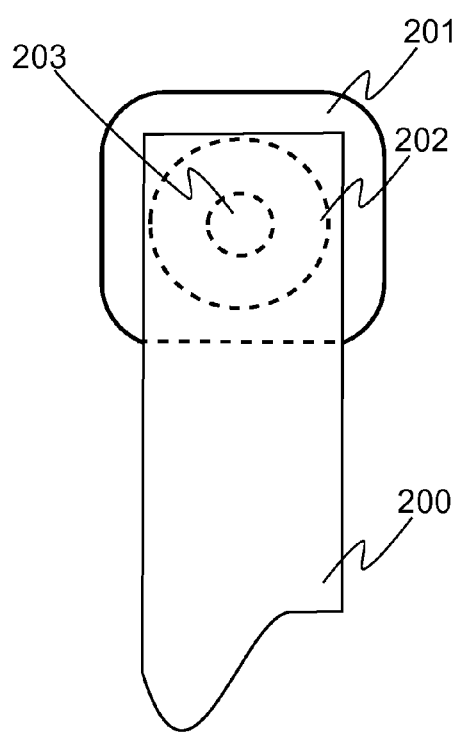
FIGS. 2a and 2b show a generalization of a typical ostomy appliance.
Figure 2:
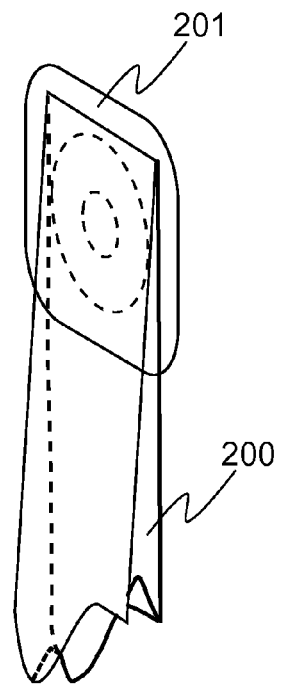

A generalized depiction from the front (FIG. 2a) and the side (FIG. 2b) of a typical ostomy appliance is shown, including a bag (200), a flange (202) which fits around a stoma (203), and a flange adhesive wafer (201) which is attached to the bag (200). As mentioned in the background of the invention section, there are a variety of ostomy appliance designs, and various methods of attaching and detaching them to and from the patient. They have in common the usage of a bag or pouch of some sort to collect the fluids and solids from the patient. Embodiments of the present invention are equally useful and applicable to all variants of ostomy appliances which employ such a pouch.

FIGS. 1a and 1b show front and side views, respectively, of one embodiment according to the present invention including a sleeve (100) through which the ostomy bag (200) is received. The sleeve is affixed (102) at one or more places to the ostomy appliance, such as by buttons, snaps, adhesive, or hook-and-loop fastener. The sleeve is also provided with at least one sensor pack (101) on at least one side (front, back, left or right), and optionally provided with a second sensor pack (not shown in these views) such as a complementary pack on an opposite side of the bag and sleeve. In other embodiments, the sleeve may be eliminated and the sensor pack may be provided directly on the bag, or the sensor pack may be provided on a dressing or other associated item (belly band, underwear, undershirt, etc.) in a position suitable for sensing the condition and events impinging on the bag.

Figure 3:
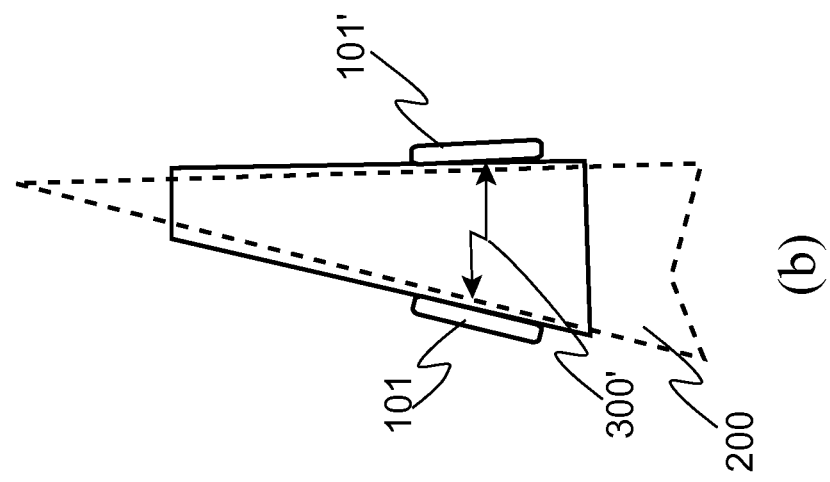
FIGS. 3a and 3b illustrate side views of an ostomy appliance in less full and fuller conditions as sensed according to the present invention.
Figure 3:
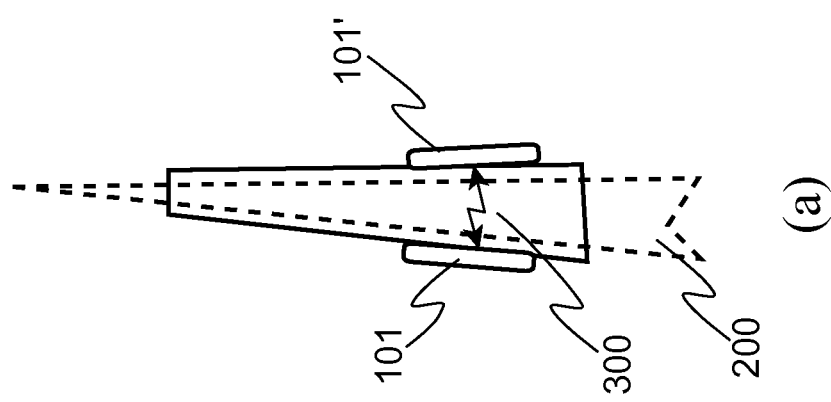

Referring now to FIG. 3a, the front sensor pack (101) and optional rear sensor pack (101') are disposed in juxtaposed positions such that suitable sensor measurements can be made into and through (300) the new, empty or less full bag (200). As the bag fills, the mass inside of it will change characteristics, which can be measured by one or more of the sensor packs, including through the bag's contents in the increased thickness (300') of the bag, as shown in FIG. 3b. Further, appropriate sensors placed in one or more of the sensor packs can measure temperature, humidity, acceleration (for impact), orientation, and movement.

Included in the sensor pack is one or more tangible, data storage memories to store the sensor data, as well as one or more data communications interfaces such as BlueTooth, Wi-Fi, IrDA, USB, etc., which would allow an external device to read the sensor data from the sensor pack(s).

Figure 4:
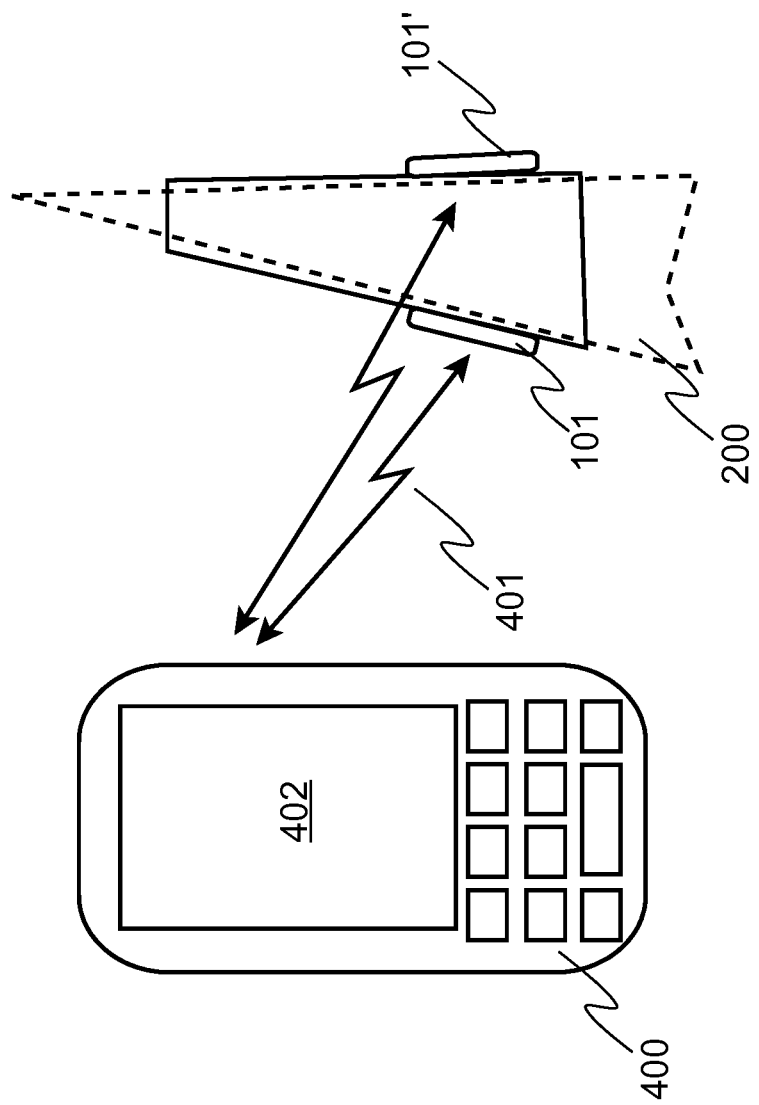
FIG. 4 illustrates data collection from the sensors according to the present invention.

Referring now to FIG. 4, a computing device (400) such as a smart phone, personal digital assistant, PocketPC, laptop computer, tablet computer, or personal computer, is equipped with a compatible data communications interface to retrieve (401) the sensor data from the sensor pack(s) (101, 101'). One or more logical processes, such as an application program ("app"), may process that retrieved sensor data, determine likely wear and fill level, and then predict when the bag should be replaced in order to avoid a failure or unplanned filled event, according to the historical data for the user and the make and model of the bag. This may be displayed (402) on the computing device, or in other embodiments, it may be communicated to a user, caregiver, or health professional through other methods such as by electronic mail, text messaging (SMS), audio alert (voice message, beep tone, chirp, etc.), or visual alert (LED, icon, etc.). For group level services, such as a floor or wing of a health care facility (nursing home, hospital, etc.), the notifications may be collected and aggregated into group reports and alerts, such as on a web page by a web server computer which is accessible by a floor nurse, wing manager, etc.

Components of an Exemplary Embodiment.

The components of one embodiment according to the present invention include a sleeve with integrated sensors (acoustic, temperature, moisture, accelerometers, optical, front to rear distance, content level, capacitive field detector, etc.), sensor data acquisition circuitry, data storage device(s), and a local communication interface module that links sensors with a smart device. The smart device, such as a smart phone, and an application program collects, analyzes and present data to the patient, and can optionally send alerts and historical data to a computing cloud.

Logical Processes and Manner of Use.

The sensor sleeve is attached to flange at typical flange clip sites in one embodiment and method of use, including attaching the sensor sleeve at a lower portion of the pouch with an additional clip to ensure proper orientation The sensor packs, and optionally the associated smart device, collects one or more of the following data points over time: temperature of the bag and contents, temperature of the user, patient orientation, bag orientation, trunk activity level (e.g. using accelerometer(s)), and trunk, leg, and chest position changes (e.g. using capacitive field detection). Other data that may be periodically collected using appropriate sensors are the liquidity level (solid versus liquid) of the pouch contents using optical or acoustic sensors, impact or shock on the pouch using accelerometers during standing, walking, jumping, etc., stress on the pouch or weight of the pouch using a strain gauge, moisture using humidity sensors, leakage detection using capacitive or conductance sensing, pouch load by separation distance between front and rear sensor packs, pouch over pressure condition by extreme separation of front and rear sensor packs, and orientation change stress (cycles of weight load occurring in vertical vs. horizontal patient positions). The integrated control unit collects the sensor data until the Smart Device connects and uploads data.

The smart device eventually collects the data which has captured patient data such as leakage events, and appliance changes over time. An application program executed by the smart device will use this data to correlate pouch use, wear and events with historical wear time and failure events to develop predictions on reduced wear time versus nominal wear time.

A user interface (UI) on the smart device, or in other embodiments on a web server or in a separate communication (email, text message, etc.), will warn the user (or a caregiver, health professional, etc.) of expected shortened wear time, prediction of leaks, possible events which may occur during the night, and will develop data to assist with planning of restocking of appliances. The application may also send data to a medical professional who can use advanced analytics to recommend changes to device usage or alternative models of device, and send alerts to registered caregivers (i.e. parent, teacher, ... ) for children who might need assistance in taking preventive action, and send data to registered caregivers for analysis of device failure linked to activities (i.e. device shows rigorous activity in the morning before failure indicating child had played football at recess).

Additionally, patterns of usage and failure over time may be determined on hourly, daily, and weekly basis. For example, a pattern of failures towards the end of the day around 4:00 pm to 5:00 pm may be detected, or a pattern of overfilling on weekends may be detected. Through this type of historical analysis, user habits, activities and schedules may be incorporated into the user alerts and predictions.

Capacitive Field Detection.

In one embodiment according to the present invention, a capacitive field detector may be employed to sense movement or activity of the wearer. While the use of accelerometers may detect some of the movement of the user by detecting movement of the pouch itself, other movements of the user which do not result in movement of the pouch may not be detected by an accelerometer on the pouch or in a sleeve.

In an embodiment employing capacitive field detection, an antenna in one or more of the sensor packs is used as part of a capacitance in a LC (inductance-capacitance) tuned oscillator such that the field around the antenna is part of a tuned oscillator circuit. As masses are moved in and out of the field around the antenna, the antenna's contribution to the capacitance of the LC oscillator changes, thereby changing the resonant frequency of the circuit. So, as a wearer's thigh moves up and down, into and out of the antenna's field, shifts in frequency of the LC circuit can be detected, thereby detecting movement of the wearer which may or may not be measured by an accelerometer on the pouch.

Such a circuit is part of a musical instrument known as a theremin, which uses two such capacitive field detectors—one to produce an output audio tone, and the other to control the volume of that output tone. In the present usage of a capacitive field detector for a movement detector according to the invention, the frequencies of use do not have to be constrained to audible frequencies of course.

Suitable Computing Platform.

The preceding paragraphs have set forth example logical processes according to the present invention, which, when coupled with processing hardware, embody systems according to the present invention, and which, when coupled with tangible, computer readable memory devices, embody computer program products according to the related invention.

Regarding computers for executing the logical processes set forth herein, it will be readily recognized by those skilled in the art that a variety of computers are suitable and will become suitable as memory, processing, and communications capacities of computers and portable devices increases. In such embodiments, the operative invention includes the combination of the programmable computing platform and the programs together. In other embodiments, some or all of the logical processes may be committed to dedicated or specialized electronic circuitry, such as Application Specific Integrated Circuits or programmable logic devices.

Figure 5:
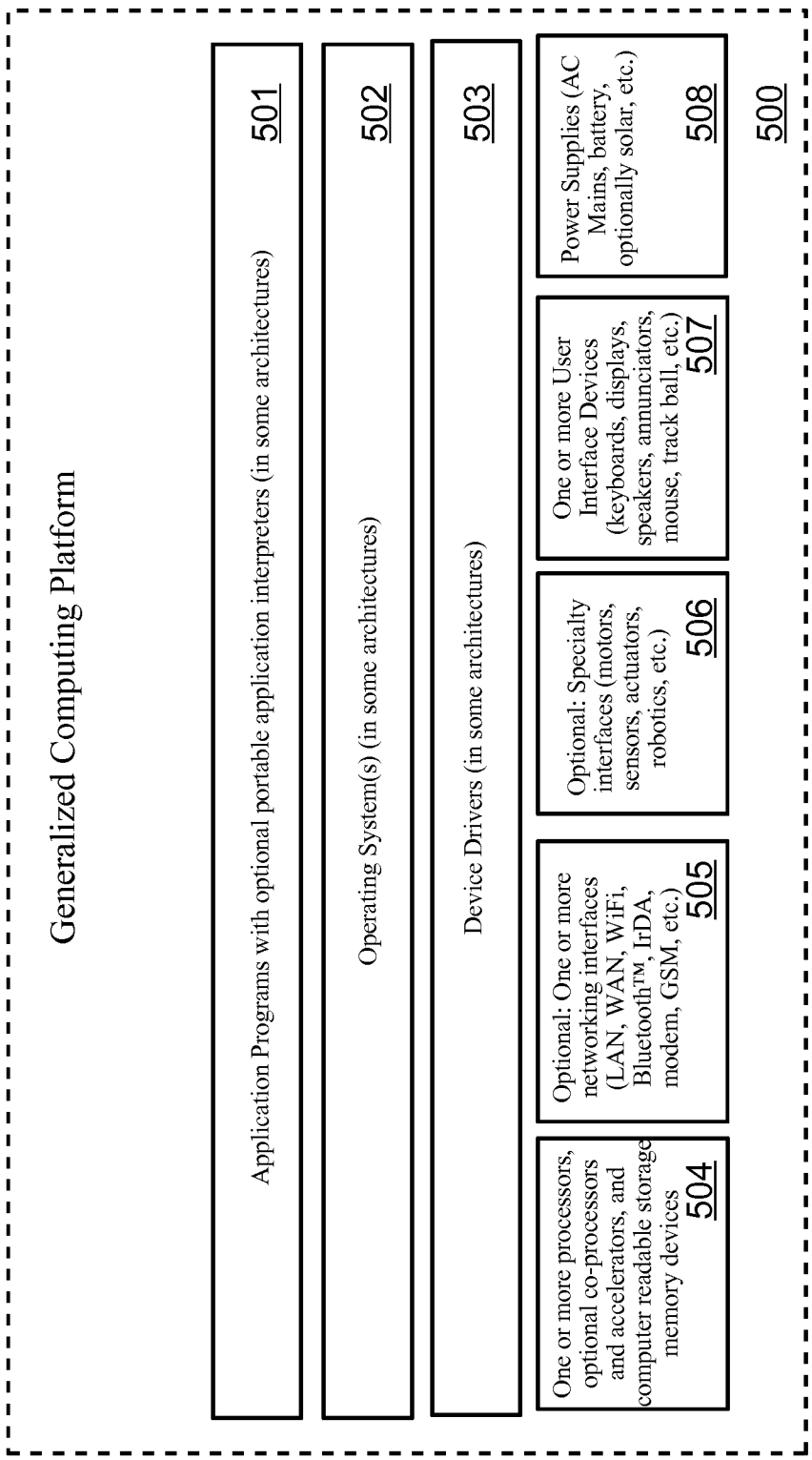
FIG. 5 sets forth a generalized computing platform suitable for realization of at least one embodiment of the present invention.

The present invention may be realized for many different processors used in many different computing platforms. FIG. 5 illustrates a generalized computing platform (500), such as common and well-known computing platforms such as "Personal Computers", web servers such as an IBM iSeries™ server, and portable devices such as personal digital assistants and smart phones, running a popular operating systems (502) such as Microsoft™ Windows™ or IBM™ AIX™, Palm OS™, Microsoft Windows Mobile™, UNIX, LINUX, Google Android™, Apple iPhone iOS™, and others, may be employed to execute one or more application programs to accomplish the computerized methods described herein. Whereas these computing platforms and operating systems are well known an openly described in any number of textbooks, websites, and public "open" specifications and recommendations, diagrams and further details of these computing systems in general (without the customized logical processes of the present invention) are readily available to those ordinarily skilled in the art.

Many such computing platforms, but not all, allow for the addition of or installation of application programs (501) which provide specific logical functionality and which allow the computing platform to be specialized in certain manners to perform certain jobs, thus rendering the computing platform into a specialized machine. In some "closed" architectures, this functionality is provided by the manufacturer and may not be modifiable by the end-user.

The "hardware" portion of a computing platform typically includes one or more processors (504) accompanied by, sometimes, specialized co-processors or accelerators, such as graphics accelerators, and by suitable computer readable memory devices (RAM, ROM, disk drives, removable memory cards, etc.). Depending on the computing platform, one or more network interfaces (505) may be provided, as well as specialty interfaces for specific applications. If the computing platform is intended to interact with human users, it is provided with one or more user interface devices (507), such as display(s), keyboards, pointing devices, speakers, etc. And, each computing platform requires one or more power supplies (battery, AC mains, solar, etc.).

Conclusion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof, unless specifically stated otherwise.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It should also be recognized by those skilled in the art that certain embodiments utilizing a microprocessor executing a logical process may also be realized through customized electronic circuitry performing the same logical process(es).

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A method for enhancing the use of and performance of ostomy appliances comprising:
   comparing, by using a computer, sensor data regarding a user, user activities, and conditions of an ostomy pouch currently being worn by the user to historical patterns of usage and failure data for the user and for a similar ostomy pouch previously worn by the user;
   in advance of a failure of the currently-worn ostomy pouch, predicting, by using a computer a reduction in nominal wear time according to the comparison; and
   notifying, by using a computer the user of the predicted reduction in nominal wear time.

2. The method as set forth in claim 1 wherein the historical patterns of usage and failure data comprises at least one record selected from the group consisting of hourly usage and failure data, daily usage and failure data, and weekly usage and failure data.

3. The method as set forth in claim 1 wherein the usage and failure data comprises data collected from at least one sensor selected from the group consisting of a thermometer for wearer temperature, a thermometer for pouch contents temperature, a pressure sensor for pouch contents, an ambient moisture detector, an ambient humidity detector, a solidity detector, a strain gauge, a pouch thickness sensor, and an accelerometer.

4. The method as set forth in claim 1 wherein the predicting of reduction in nominal wear time comprises one or more analyses selected from the group consisting of movement activity analysis, shock analysis, impact analysis, moisture analysis, pressure analysis, fill rate analysis, temperature analysis, orientation stress analysis, hourly analysis, daily analysis, and weekly analysis.

5. The method as set forth in claim 1 wherein the prediction of reduced wear time of the pouch consists of a reduction based on one or more predictions selected from the group consisting of a failure of the pouch prior to scheduled replacement, a filling of the pouch prior to scheduled emptying, and a weakening of the pouch during nominal wear time.

6. The method as set forth in claim 1 further comprising providing one or more sensors to the ostomy pouch in a sleeve through which is formed a channel for receiving the ostomy pouch, and disposing one or more sensors on the sleeve in a position to make one or more measurements on the pouch, the wearer, or both the pouch and wearer.

7. The method as set forth in claim 6 wherein attachment points are provided to the sleeve for affixing the sleeve to an ostomy appliance to achieve a known orientation.

8. The method as set forth in claim 1 further comprising providing one or more sensors onto or into the ostomy pouch.

9. The method as set forth in claim 1 further comprising providing two or more sensors to the ostomy pouch in a juxtapositioned arrangement whereas one or more measurements may be made through, around or about the ostomy pouch.

10. The method as set forth in claim 1 wherein the notifying comprises at least one communications selected from the group consisting of an electronic mail message, a text message, a visual alert, an audible alert, and a portion of an aggregated report for a plurality of ostomy appliance wearers.

11. A computer program product for enhancing the use of and performance of ostomy appliances comprising:
    a tangible, computer-readable data storage memory device;
    one or more program instructions embodied by the memory device for causing a processor to, when executed, perform operations comprising:
      comparing sensor data regarding a user, user activities, and conditions of an ostomy pouch currently being worn by the user to historical patterns of usage and failure data for the user and for a similar ostomy pouch previously worn by the user;
      in advance of a failure of the currently-worn ostomy pouch, predicting a reduction in nominal wear time according to the comparison; and
      notifying the user of the predicted reduction in nominal wear time.

12. The computer program product as set forth in claim 11 wherein the patterns of usage and failure data comprises at least one data selected from the group consisting of hourly usage and failure data, daily usage and failure data, weekly usage and failure data, a thermometer for wearer temperature, a thermometer for pouch contents temperature, a pressure sensor for pouch contents, an ambient moisture detector, an ambient humidity detector, a solidity detector, a strain gauge, a pouch thickness sensor, and an accelerometer.

13. The computer program product as set forth in claim 11 wherein the program instruction for predicting comprises program instruction code for performing one or more analyses selected from the group consisting of movement activity analysis, shock analysis, impact analysis, moisture analysis, pressure analysis, fill rate analysis, temperature analysis, orientation stress analysis, hourly analysis, daily analysis, and weekly analysis, predicting failure of the pouch prior to scheduled replacement, predicting filling of the pouch prior to scheduled emptying, and predicting weakening of the pouch during nominal wear time.

14. The computer program product as set forth in claim 11 wherein the program instruction for notifying comprises program instruction for performing at least one communications selected from the group consisting of an electronic mail message, a text message, a visual alert, an audible alert, and a portion of an aggregated report for a plurality of ostomy appliance wearers.

15. A system for enhancing the use of and performance of ostomy appliances comprising:
    a computer processor;
    a tangible, computer readable storage memory device excluding a propagating signal; and
    program instructions embodied by the memory device for causing the processor to perform operations of:
      comparing sensor data regarding a user, user activities, and conditions of an ostomy pouch currently being worn by the user to historical patterns of usage and failure data for the user and for a similar ostomy pouch previously worn by the user;
      in advance of a failure of the currently-worn ostomy pouch, predicting a reduction in nominal wear time according to the comparison; and
      notifying the user of the predicted reduction in nominal wear time.

16. The system as set forth in claim 15 wherein the patterns of usage and failure data comprises at least one data selected from the group consisting of hourly usage and failure data, daily usage and failure data, weekly usage and failure data, a thermometer for wearer temperature, a thermometer for pouch contents temperature, a pressure sensor for pouch contents, an ambient moisture detector, an ambient humidity detector, a solidity detector, a strain gauge, a pouch thickness sensor, and an accelerometer.

17. The system as set forth in claim 15 wherein the program instruction for predicting comprises program instruction for performing one or more analyses selected from the group consisting of movement activity analysis, shock analysis, impact analysis, moisture analysis, pressure analysis, fill rate analysis, temperature analysis, orientation stress analysis, hourly analysis, daily analysis, weekly analysis.

18. The system as set forth in claim 15 wherein the program instruction for prediction comprises program instruction for performing one or more predictions selected from the group consisting of a failure of the pouch prior to scheduled replacement, a filling of the pouch prior to scheduled emptying, and a weakening of the pouch during nominal wear time.

19. The system as set forth in claim 15 further comprising one or more of the sensors affixed to a sleeve through which is formed a channel for receiving the ostomy pouch, in one or more positions to make one or more measurements on the pouch, the wearer, or both the pouch and wearer.

20. The system as set forth in claim 15 wherein the program instruction for notifying further comprises program instruction for performing at least one communications selected from the group consisting of an electronic mail message, a text message, a visual alert, an audible alert, and a portion of an aggregated report for a plurality of ostomy appliance wearers.

* * * * *